US009452262B2

(12) United States Patent
Pommerau et al.

(10) Patent No.: US 9,452,262 B2
(45) Date of Patent: *Sep. 27, 2016

(54) DRUG DELIVERY DEVICE AND ASSOCIATED PACKAGING

(71) Applicant: SANOFI-AVENTIS DEUTSCHLAND GMBH, Frankfurt am Main (DE)

(72) Inventors: Christian Pommerau, Frankfurt am Main (DE); Anke Liewald, Frankfurt am main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/623,126

(22) Filed: Feb. 16, 2015

(65) Prior Publication Data

US 2015/0157798 A1    Jun. 11, 2015

Related U.S. Application Data

(63) Continuation of application No. 13/508,844, filed as application No. PCT/EP2010/068593 on Dec. 1, 2010, now Pat. No. 8,968,254.

(30) Foreign Application Priority Data

Dec. 2, 2009   (EP) .................................... 09177683

(51) Int. Cl.
*A61M 5/24*   (2006.01)
*A61J 1/06*   (2006.01)
(Continued)

(52) U.S. Cl.
CPC ................ *A61M 5/24* (2013.01); *A61J 1/062* (2013.01); *A61M 5/31551* (2013.01); *A61M 5/31585* (2013.01); *A61J 2200/72* (2013.01); *A61J2205/20* (2013.01); *A61M 2005/3125* (2013.01); *A61M 2005/3126* (2013.01); *A61M 2205/0238* (2013.01); *A61M 2205/27* (2013.01); *A61M 2205/3368* (2013.01); *A61M 2205/583* (2013.01); *A61M 2205/584* (2013.01); *A61M 2209/06* (2013.01)

(58) Field of Classification Search
CPC .. A61J 1/062; A61J 2200/72; A61J 2205/20; A61M 2005/3125; A61M 2005/3126; A61M 2205/0238; A61M 2205/27; A61M 2205/3368; A61M 2205/583; A61M 2205/584; A61M 2209/06; A61M 5/24; A61M 5/31551; A61M 5/31585
See application file for complete search history.

(56) References Cited

U.S. PATENT DOCUMENTS 4,179,397 A    12/1979  Rohowetz et al.
5,085,801 A    2/1992   Thierry et al.
(Continued)

FOREIGN PATENT DOCUMENTS

DE    WO2006037435    *   9/2005
WO    01/70309            9/2001
(Continued)

*Primary Examiner* — Imani Hayman
(74) *Attorney, Agent, or Firm* — McDonnell Boehnen Hulbert & Berghoff LLP

(57) ABSTRACT

The present invention relates to a drug delivery device and in particular to temperature sensitive labelling of such devices. The drug delivery device is designed for dispensing of a dose of a medicinal product and includes a housing, and a drive mechanism comprising an axially displaceable piston rod to act on a piston of a cartridge containing the medicinal product to be dispensed. The device is further provided with an indicator adapted to irreversibly change at least one of its visually perceptible properties in response to the ambient temperature rising above and/or dropping below at least one predefined threshold. The indicator is preferably designed as a protective cover arranged across a functional component of the device.

6 Claims, 2 Drawing Sheets

(51) Int. Cl.
*A61M 5/315* (2006.01)
*A61M 5/31* (2006.01)

(56) References Cited

U.S. PATENT DOCUMENTS

| | | |
|---|---|---|
| 2005/0131355 A1 | 6/2005 | Kirchhofer et al. |
| 2008/0177246 A1 | 7/2008 | Sullivan et al. |
| 2009/0312713 A1 | 12/2009 | Greutert et al. |
| 2012/0130316 A1 | 5/2012 | Boyd et al. |

FOREIGN PATENT DOCUMENTS

| | | |
|---|---|---|
| WO | 01/72601 | 10/2001 |
| WO | 2008/041146 | 4/2008 |
| WO | 2008/146021 | 12/2008 |

* cited by examiner

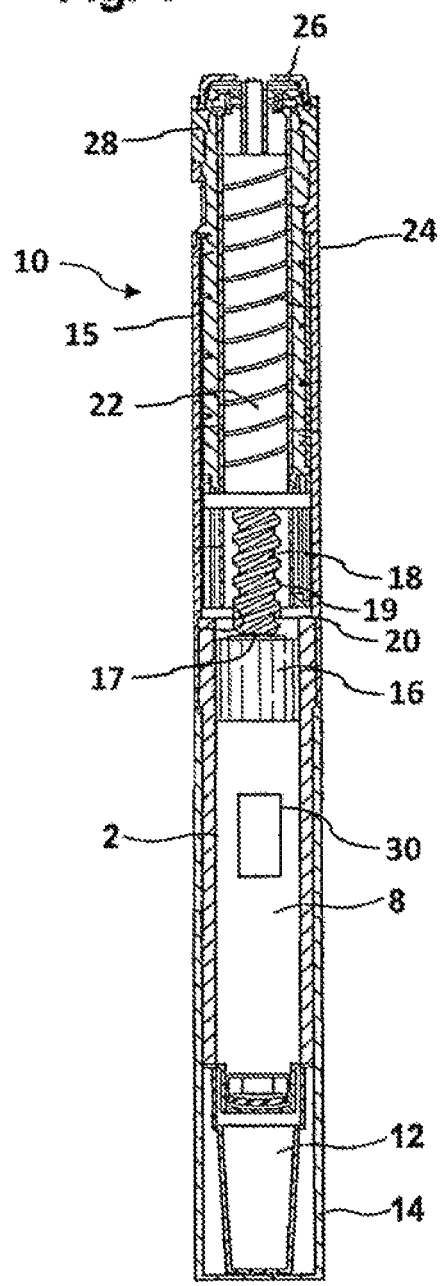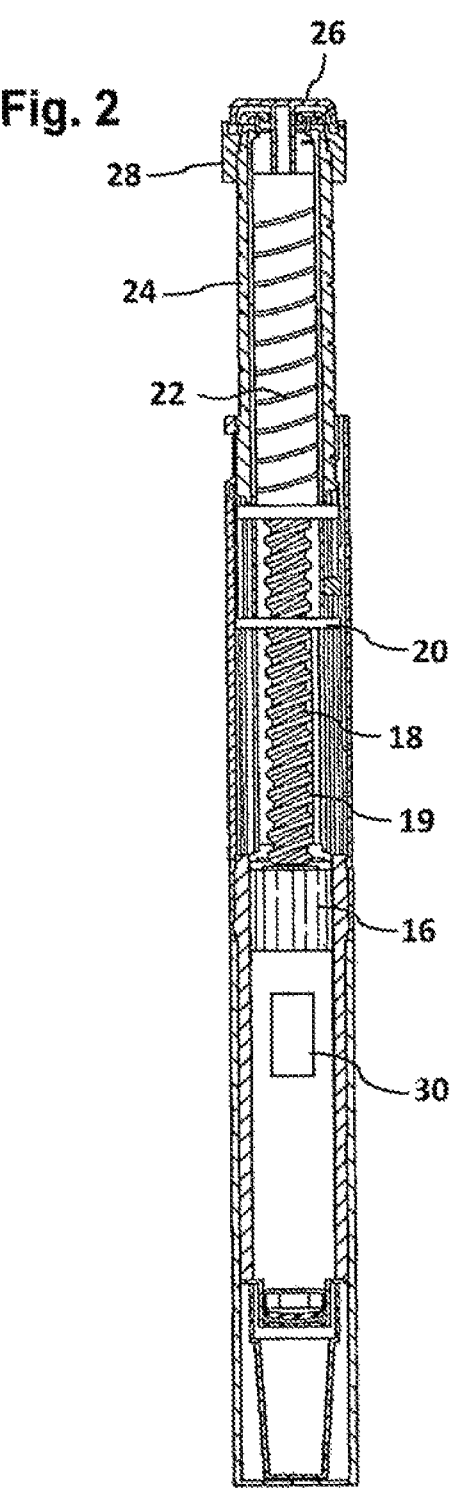

DRUG DELIVERY DEVICE AND ASSOCIATED PACKAGING

CROSS REFERENCE TO RELATED APPLICATIONS

The present application is a continuation of U.S. patent application Ser. No. 13/508,844, filed Sep. 27, 2012, now U.S. Pat. No. 8,968,254 which is a U.S. National Phase Application pursuant to 35 U.S.C. §371 of International Application No. PCT/EP2010/068593 filed Dec. 1, 2010, which claims priority to European Patent Application No. 09177683.1 filed Dec. 2, 2009. The entire disclosure contents of these applications are herewith incorporated by reference into the present application.

DESCRIPTION

The present invention relates to drug delivery devices such as pen-type injectors, which allow administering a single or a number of pre-set doses of a medicinal product. In particular, the invention relates to such drug delivery devices that are designed and configured for self-administration, hence to be directly handled by a patient.

BACKGROUND

Drug delivery devices allowing for multiple dosing of a required dosage of a liquid medicinal product, such as liquid drugs, and further providing administration of the liquid to a patient, are as such well-known in the art. Generally, such devices have substantially the same purpose as that of an ordinary syringe.

Pen-type injectors of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

Some medicinal products, for instance insulin, heparin or growth hormones have to be stored in a refrigerated environment in order to prevent disintegration or decomposition. Some medicinal products that are typically subject to self-administration may even rapidly decompose when exposed to ambient temperatures above an admissible threshold. Since handling and storage of such drug delivery devices and associated medicinal products is entirely in the responsibility of the patient himself, there exists a significant risk to health, when for instance the medicinal product has not been stored properly prior to administration.

Administering a dose of a medicinal product that has been improperly stored or otherwise improperly treated may lead to severe consequences for the health of the patient. Even a short-term and singular rise of the ambient temperature may lead to a substantial disintegration of a medicinal product, which is unfortunately not visible to the end user. In such cases, where the user is not aware that a critical rise in temperature has occurred, the user has no reason to believe, that the medicinal product might be substantially ineffective or even harmful.

Additionally, even in such cases, where the user has become aware of an at least temporally improperly stored medicinal product and/or medical device, the user, due to a lack of experience, may play down the potential harmful effect of improperly stored drugs and/or devices.

In any case, the user or patient may be exposed to a considerable risk to health, once a drug delivery device and/or a cartridge containing a respective medicinal product has been improperly stored or otherwise improperly treated.

It is therefore an object of the present invention to provide an improved drug delivery device together with an improved packaging and/or an improved cartridge that minimize the risk of injecting a medicinal product that has been subject to improper storage or otherwise improper treatment. It is therefore another object of the present invention to provide an effective means to enhance patient safety and to improve the general handling of drug delivery devices and associated components such as packaging and/or cartridges providing the medicinal product.

SUMMARY

The present invention provides a drug delivery device for dispensing of a dose of a medicinal product. The drug delivery device is preferably designed as a pen-type injector providing injection and administration of a single or of multiple pre-set doses of a medicinal product. The drug delivery device comprises at least a housing component and a drive mechanism, wherein the drive mechanism comprises an axially displaceable piston rod. The piston rod is adapted to act on a piston of a cartridge to be inserted into the drug delivery device.

Depending on whether the drug delivery device is designed as a reusable or disposable device, the cartridge can be removably arranged in a cartridge holder of the drug delivery device. The cartridge contains the medicinal product to be dispensed and further comprises a piston slidably disposed therein. The cartridge is typically designed as a carpule or vial. It may also be configured as an ampoule or syringe. The axially displaceable piston rod of the drive mechanism is adapted to apply distally directed thrust to the piston in order to expel a pre-defined amount of the medicinal product during a dose dispensing procedure.

The drug delivery device according to the present invention is further provided with an protective cover serving as an indicator means and which is adapted to irreversibly change at least one of its visually perceptible properties in response to the ambient temperature rising above and/or dropping below at least one given predefined threshold, which is typically defined by the type and composition of the medicinal product.

Preferably, the protective cover increases its degree of opacity and decreases its degree of transparency in response of the ambient temperature crossing the predefined threshold.

Furthermore, the protective and temperature sensitive cover is arranged across a functional component of the drug delivery device that visually provides information about the device status and/or about the cartridge. When the protective cover becomes substantially non-transparent, said information of the functional component is no longer discernible for a user and the entire device becomes useless. In the present context, a functional component is either a part of the drive mechanism and/or may display device specific information to the end user. The functional component may comprise a dose selecting window and/or may comprise a window embedded in a cartridge holder section of the drug delivery device, thereby providing visual access to a scale disposed on a cartridge arranged therein.

This way, the drug delivery device turns itself inoperable as soon as the ambient temperature reaches a level which is non-suitable for the medicinal product stored therein.

By providing a temperature-sensitive protective cover irreversibly modifying its outer appearance, an effective labelling of the drug delivery device can be provided indicating to the end user, that the device and/or the medicinal product contained therein should no longer be used. By means of the irreversible change in transparency, the protective cover according to the present invention is indicative that the medicinal product and/or the drug delivery device has or have been subject to an inadmissible temperature, at which the medicinal product may have partially decomposed.

By having the protective cover directly attached to the drug delivery device, a patient or end user can be directly informed about a potential danger to health.

The at least one protective cover may be adapted to exclusively respond to a rise in temperature above a predefined upper threshold. Additionally, another or the same protective cover may accordingly be adapted to visually respond to a dropping of the ambient temperature beneath a lower threshold, which may for instance be characterized by a temperature, at which the chemical or physical consistency of the medicinal product does not allow for proper administration, hence injection of the medicinal product.

According to a preferred embodiment of the invention, the protective cover irreversibly changes its colour in response to the ambient temperature crossing the at least one temperature threshold. In this way, the indicator means may change from an initial colour to a first colour, e.g. when the ambient temperature rises above an upper threshold. Additionally and/or alternatively, the protective cover may feature a different, second colour when the ambient temperature drops below a lower threshold. Said changes in colour are typically accompanied with a respective change in transparency and/or opacity. In this way, an end user can even be informed about the type of threshold, the ambient temperature has crossed.

Providing of different colours indicating a crossing of upper and/or lower temperature thresholds can for instance be implemented by making use of a plurality of protective covers being configured respectively.

It is of further advantage, when the protective cover itself is implemented or embedded in a visible component of the drug delivery device. In this context, a visible component of the drug delivery device is a component being visible by the end user in any conceivable configuration of the device. If, for instance, the protective cover is implemented in a housing component of the drug delivery device and if said component is configured substantially transparent, rising or falling of the ambient temperature across the at least one threshold may lead to a substantial change, typically to an increase in opacity of said housing component.

Hence, due to a rise in temperature above an upper admissible threshold, said housing component can irreversibly change its degree of transparency and may thus cover or hide relevant information required to operate the drug delivery device. In this way, further use of the drug delivery device can almost entirely be prevented as soon as the ambient temperature has at least once traversed a given temperature threshold.

According to a further preferred embodiment of the invention, the protective cover is configured as a coating or as a label attached to an outer surface of the drug delivery device or to components thereof. Hence, the protective cover may be universally applied to any suitable device component, such as a main housing component, a cartridge holder or even to a removable cap of the device, e.g. in form of a coating or by way of an adhesive label. Making use of a temperature-sensitive coating or a respective adhesive label may also be beneficial for a production and assembly process of such drug delivery devices. Coatings or labels may be applied to a drug delivery device after its assembly has been completed.

Hence, temperature-sensitive labelling of a drug delivery device may be conducted after termination of an assembly procedure, which itself is therefore generally not affected by the temperature sensitive labelling.

In a further preferred embodiment of the invention, the protective cover comprises at least one thermochromic additive. Such additives can be provided for instance in form of thermochromic pigments, microencapsulated particles and/or by way of nanoparticles having a geometric size in the molecular range.

Thermochromic pigments can for instance be applied in form of a coating, by way of an adhesive label and/or in form of an additive embedded in the bulk of a component of the drug delivery device. The thermochromic additive may further be mixed with other colour pigments allowing to modify the appearance of a respective device component according to given design requirements. Moreover, by combining colour pigments and suitable thermochromic pigments, clearly indicative temperature changes can be implemented that will not leave any doubt to the user of the device once the predefined temperature threshold has been crossed.

Furthermore, and according to another preferred embodiment of the invention, the protective cover is visibly embedded in or is attached to a dose indicating unit, a cartridge holder, a removable cap, a dose dial button, a dose inject button and/or a dial grip of the drug delivery device. Said components, typically visibly disposed to the user are particularly suitable to indicate, that the device and/or the medicinal product contained therein should no longer be used. Also a replaceable needle assembly to be interconnected with the cartridge holder can be provided with the above described temperature-sensitive protective cover.

In a further preferred embodiment, the protective cover is arranged at least across a dose displaying window. The dose displaying window and the protective cover, which is initially substantially transparent, allow a user to control the size of a set dose. By embedding thermochromic additives for instance into the protective cover, its degree of transparency may drastically decrease and said protective cover may become entirely opaque when the ambient temperature crosses the at least one pre-defined threshold. In this case, the opacity-increased protective cover hinders an end user in reading relevant dose information, which is required for dispending of a pre-defined dose. Hence, by appropriately colouring a protective cover, the entire device substantially becomes unusable.

Also, and according to a further aspect the protective cover becomes substantially opaque and/or non-transparent, once the ambient temperature traverses the predefined threshold.

In still another embodiment, the drug delivery device comprises a cartridge filled with the medicinal product. The drug delivery device may be designed as a disposable device and may be readily equipped with a filled cartridge. Instead of replacing an empty cartridge, the device itself can be discarded.

In another aspect, the invention further relates to a packaging for a drug delivery device, wherein the packaging comprises an indicator means or a protective cover adapted to irreversibly change at least one of its visually perceptible properties in response to the ambient temperature rising above and/or dropping below at least one pre-defined temperature threshold. Correspondingly as described above for the drug delivery device, also a packaging adapted to protect such drug delivery devices or components thereof can be equipped with a temperature sensitive indicator means.

The packaging may comprise a package made of paper or cardboard. By having the protective cover or indicator means on the packaging, an end user may even be informed of improper storage of such a drug delivery device even before unwrapping or opening said packaging. Also for vendors and suppliers, such an indicator means helps to detect weak points in a cold chain e.g. required for transportation of the device from the manufacturer to patients or to end consumers.

In a further embodiment, the packaging may be configured as an at least partially transparent packaging film or foil, in which the drug delivery device is for instance shrink-wrapped. Such packaging film or packaging foil may also change its degree of opacity and/or its degree of transparency when exposed to an ambient temperature lying outside the predefined and admissible temperature range. Here, it may already be sufficient, if only parts of the at least partially transparent packaging film are provided with e.g. a coating comprising thermochromic pigments and/or additional colour pigments.

In still another and independent aspect, the invention further relates to a cartridge to be used with a drug delivery device. Here, the cartridge wall comprises a temperature sensitive indicator means provided with a protective cover or with a respective coating adapted to irreversibly change increase its degree of transparency and/or opacity in response to the ambient temperature rises above and/or below a predefined threshold. In particular, the cartridge wall, e.g. made of glass, may be coated with a thermochromic additive, irreversibly changing its colour and/or transparency such that for instance a scale disposed underneath is no longer readable when the ambient temperature rises above or falls below a predefined threshold. Additionally, also the thermochromic, colour- or transparency-changing additive can be embedded in the bulk of the material forming the cartridge wall.

It is of further advantage when the cartridge comprises a scale indicating the filling level of the cartridge and when the protective cover or coating becomes substantially non-transparent when the ambient temperature traverses or crosses the at least one predefined temperature threshold. This way, the cartridge becomes non-usable if once exposed to unsuitable thermal conditions.

By providing not only the drug delivery device but also a cartridge with a temperature sensitive indicator means, the invention can be universally applied not only to disposable but also to reusable drug delivery devices, wherein cartridges filled with the medicinal product to be dispensed can after usage be replaced by a new cartridge. Providing such replaceable cartridges with a temperature sensitive indicator means is beneficial for a surveillance of compliances in a cold logistic chain of such cartridges.

Generally, the temperature sensitive protective cover is not only to be used with drug delivery devices such like pen-type injectors but also with inhalers or the like devices.

The term "medicament" or "medicinal product", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-litho-cholyl-Y-glutamyl)-des(B30) human insulin; B29-N-(w-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39), des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5-des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be apparent to those skilled in the pertinent art that various modifications and variations can be made to the present invention without departing from its spirit and scope. Further, it is to be noted, that any reference signs used in the appended claims are not to be construed as limiting the scope of the present invention. It is further to be noted, that the present invention can be universally applied and implemented with numerous medical devices as well as to different methods focussing on labelling and/or visualizing an unusability of medical devices, and in particular of drug delivery devices, such as pen-type injectors.

BRIEF DESCRIPTION OF THE FIGURES

Without limitation, the present invention will be explained in greater detail below in connection with preferred embodiments and with reference to the drawings in which:

FIG. 1 shows a drug delivery device in cross section in an initial configuration and FIG. 2 illustrates the drug delivery device according to FIG. 1 prior dose dispensing and FIG. 3 shows another embodiment of a pen-type injector comprising a display window.

DETAILED DESCRIPTION

Figure 3:
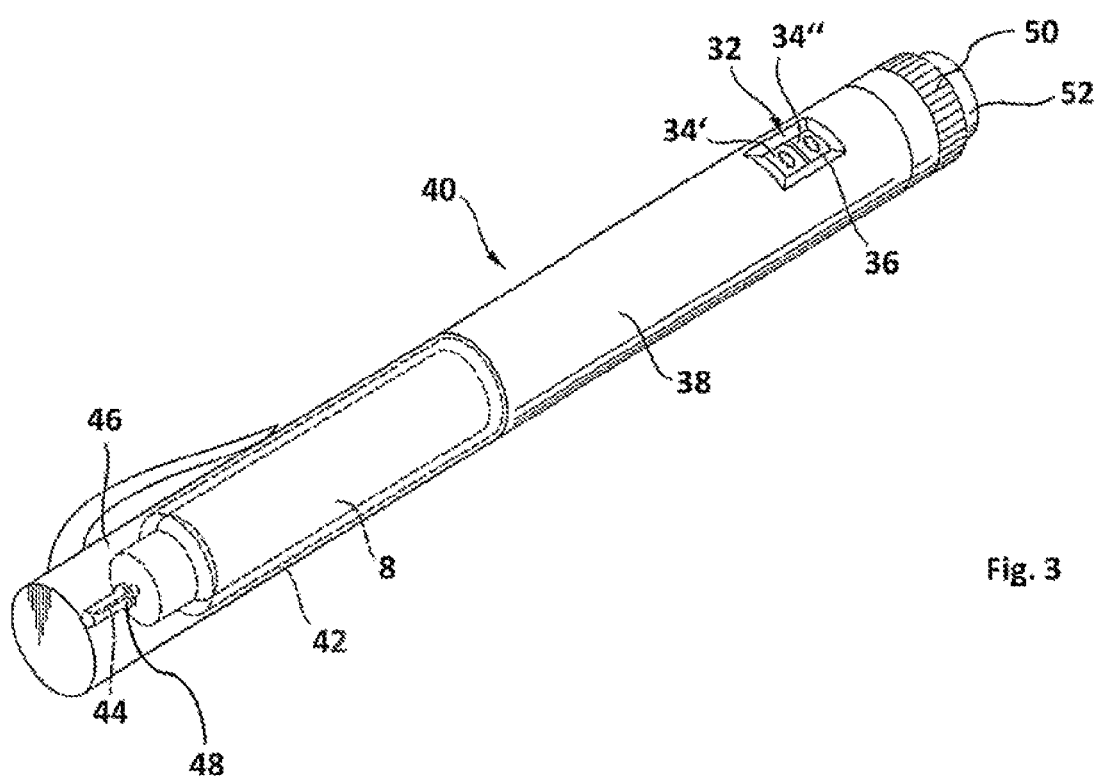

The drug delivery device 4 as illustrated in FIGS. 1 and 2 comprises a cartridge holder 2 that serves to house and to receive a cartridge 8 filled with a medicinal product to be dispensed by the drive mechanism 10 of the drug delivery device 4. The cartridge 8 comprises at its upper, hence proximal end section a piston 16 moveably disposed in said cartridge 8. A removable cap 12 is releasably retained at a lower, distal end of the cartridge holder 2. In use, said cap 12 can be replaced by a suitable piercing element, such an injection needle, cannula or the like for dispensing and administering the liquid drug to a patient.

The entire cartridge holder 2 is further covered by another replaceable cap 14. Preferably, the outer dimensions of said replaceable cap 14 are similar or identical to the outer dimensions of a main housing component 15, which serves to accommodate the drive mechanism 10.

The drive mechanism 10 comprises a piston rod 18 having an outer thread 19 matching with an inner thread of an axially displaceable insert or lead screw 20. Moreover, the piston rod 18 is also threadedly engaged with an inner thread of an axially displaceable drive sleeve 22. Said piston rod 18 comprises a second threaded portion at its upper, proximal end section, which is not explicitly illustrated in the Figures. With its second threaded portion, it is threadedly engaged with the inner thread of the drive sleeve 22.

The piston rod 18 comprises a pressure piece 17 at its lower, hence distal, end section, which buts against a proximal end face of the piston 16 of the cartridge 8. In this way, distally directed thrust provided by the piston rod 18 is transferred to a respective distally directed movement of the piston 16, thereby expelling a pre-defined amount of the liquid medicinal product contained in the cartridge 8.

Preferably, first and second threads of the piston rod 18 are oppositely directed and comprise different leads. In this way, an axial displacement of the drive sleeve 22 leads to a rotational movement of the piston rod, which due to the threaded engagement with the insert 20 becomes also subject to a respective axial displacement in distal direction, hence, towards the lower part of the drug delivery device 4.

As illustrated in FIGS. 1 and 2, the drive mechanism 10 further comprises a dose dial sleeve 24 as well as a dose dial button 28, by means of which the drive mechanism 10 can be transferred into a configuration as illustrated in FIG. 2, wherein the drive sleeve 22 and the dose dial sleeve 24 together with the dose dial button 28 and a dose button 26 axially protrude from the housing 15 of the drive mechanism 10.

Starting from the configuration as illustrated in FIG. 2, a user may manually exert distally directed thrust to the dose button 26, which consequently leads to an axially and distally directed displacement of the entire drive mechanism 10. Due to the threaded engagement of the piston rod 18 with both, the drive sleeve 22 and the insert 20, distally directed movement of the piston rod 18 is reduced compared to the distally directed displacement of the drive sleeve 22.

Any one or several of the illustrated parts and components of the drug delivery device 4 according to FIGS. 1 and 2 that are visible to a user can be provided with a protective cover 30 according to the present invention. In the illustrated embodiment of FIGS. 1 and 2, the cover 30 is configured as a surface element arranged on the outer circumference of a cartridge holder 2. Generally, also the removable caps 12, 14, the main housing component 15, the dose dial button 28 as well as the dose inject button 26 can be provided with or can even be entirely configured as a protective cover being adapted to irreversibly change its degree of opacity and/or transparency in response to the ambient temperature rising above and/or dropping below at least one predefined threshold. In the embodiment as illustrated in FIGS. 1 and 2, the cover or window 30 is arranged across a window section of the cartridge holder 2 and provides visual access to the cartridge 8 disposed therein. Here, the cartridge and in particular its scale serves as a functional component.

Moreover, also a dose dial sleeve 24 axially extending from the main housing component 15 as illustrated in FIG. 2 can be regarded as functional component to be equipped with a temperature-sensitive protective cover providing a temperature-sensitive indicating means. Since the dose dial sleeve 24 is further provided with dose-related size information, a colour change or a change in opacity and/or in transparency may lead to a general unusability of the drug delivery device 4. If for instance a thermochromic coating covering a scale of the dose dial sleeve 24 becomes subject to a decrease in its degree of transparency, the scale providing important information for setting and/or dispensing of a dose will be no longer readable by the end user.

In preferred embodiments, the protective cover is subject to a change in colour towards particular signal colours, such as red or comparable bright colours clearly indicating, that the drug delivery device and/or its medicinal product should no longer be used.

In the embodiment according to FIG. 3, another drug delivery device 40 is illustrated. This device 40 is also of pen-injector type. It comprises a main housing component 38 and a cartridge holder 42, adapted to hold a replaceable cartridge 8, which is filled with the medicinal product to be dispensed by the device 40. Also here, the cartridge holder 42 is covered by a replaceable cap 46. At the distal end portion of the cartridge holder 42, a needle assembly 45 protected by a needle cap 48 is further illustrated.

The main housing component 38 serves to house a drive mechanism, which is not further illustrated here. Further, the main housing component 38 comprises a through opening in form of a dose dial window 36. By rotating the dose dial 50, the rotating digits 34' and 34" will indicate the size of a dose being actually set and prepared for a subsequent dispensing procedure. After setting of a respective dose, by depressing of a dose inject button 52, the drive mechanism applies respective thrust to the piston of the cartridge 8 and a well-defined amount of the medicinal product can be administered.

In the embodiment according to FIG. 3, the protective cover 32 is arranged across the window 36 of the main housing component 38. In an initial configuration, the protective cover 32 is substantially transparent and allows reading of the dose-size related information as given by the digits 34', 34". However, as soon as the ambient temperature drops below or exceeds across at least one lower or an upper threshold, the protective cover 32 may change its colour and/or may change its degree of transparency and/or opacity, respectively. In this way, the user can be intuitively informed, that the device has been subject to an improper storage. Moreover, when the protective cover 32 becomes almost opaque, reading of the digits 34', 34" becomes almost impossible for the user and the entire device 40 becomes practically unusable.

The invention claimed is:
1. A drug delivery device for dispensing of a user settable dose of a medicinal product, comprising:
  a housing, and
  a drive mechanism comprising an axially displaceable piston rod to act on a piston of a cartridge containing the medicinal product to be dispensed,
  wherein the drug delivery device is further provided with a protective cover attached across a dose indicating unit of the drug delivery device, the dose indicating unit indicating the size of a user settable dose,
  wherein the protective cover is adapted to irreversibly increase a degree of opacity and to decrease a degree of transparency in response to an ambient temperature rising above or dropping below at least one predefined threshold, wherein the protective cover is substantially transparent prior to the ambient temperature crossing the at least one threshold, so that the user settable dose is viewable, and wherein the protective cover becomes and remains substantially non-transparent in response to a crossing of the ambient temperature above or below the at least one predefined threshold, so that the user settable dose is no longer viewable.

2. The drug delivery device according to claim 1, wherein the protective cover irreversibly changes color in response to the ambient temperature crossing the at least one threshold.

3. The drug delivery device according to claim 1, wherein the protective cover is implemented or embedded in a housing component of the device.

4. The drug delivery device according to claim 1, wherein the protective cover is a surface element.

5. The drug delivery device according to claim 1, wherein the protective cover comprises at least one thermochromic additive.

6. The drug delivery device according to claim 1, wherein the cartridge is filled with the medicinal product.

* * * * *